(12) United States Patent
Kitagawa

(10) Patent No.: US 9,172,227 B2
(45) Date of Patent: Oct. 27, 2015

(54) WIRE GUIDE MEMBER

(71) Applicant: OLYMPUS CORPORATION, Tokyo (JP)

(72) Inventor: Hideya Kitagawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 341 days.

(21) Appl. No.: 13/728,233

(22) Filed: Dec. 27, 2012

(65) Prior Publication Data

US 2013/0112457 A1    May 9, 2013

Related U.S. Application Data

(63) Continuation of application No. PCT/JP2011/065800, filed on Jul. 11, 2011.

(30) Foreign Application Priority Data

Aug. 23, 2010    (JP) .................................. 2010-186241

(51) Int. Cl.
| | | |
|---|---|---|
| *A61B 1/00* | (2006.01) | |
| *H02G 3/04* | (2006.01) | |
| *A61B 1/005* | (2006.01) | |
| *A61B 1/008* | (2006.01) | |

(52) U.S. Cl.
CPC ................ *H02G 3/04* (2013.01); *A61B 1/0056* (2013.01); *A61B 1/0057* (2013.01); *A61B 1/008* (2013.01); *A61B 1/0052* (2013.01)

(58) Field of Classification Search
USPC ................................................ 600/139–151
See application file for complete search history.

(56) References Cited

U.S. PATENT DOCUMENTS

| | | | | |
|---|---|---|---|---|
| 3,610,231 A * | 10/1971 | Takahashi et al. | ............ | 600/139 |
| 4,748,969 A * | 6/1988 | Wardle | ............ | 600/150 |
| 4,787,369 A * | 11/1988 | Allred et al. | ............ | 600/149 |
| 4,905,666 A * | 3/1990 | Fukuda | ............ | 600/146 |
| 5,179,935 A * | 1/1993 | Miyagi | ............ | 600/142 |
| 5,531,664 A * | 7/1996 | Adachi et al. | ............ | 600/149 |
| 7,591,783 B2 * | 9/2009 | Boulais et al. | ............ | 600/142 |

(Continued)

FOREIGN PATENT DOCUMENTS

| | | |
|---|---|---|
| JP | 57-119059 | 7/1982 |
| JP | 58-46801 Y2 | 10/1983 |

(Continued)

OTHER PUBLICATIONS

International Search Report dated Oct. 18, 2012 (in English) in counterpart International Application No. PCT/JP2011/065800.
International Preliminary Report on Patentability (IPRP) dated Mar. 28, 2013 (in English) issued in parent International Application No. PCT/JP2011/065800.

*Primary Examiner* — Matthew J Kasztejna
(74) *Attorney, Agent, or Firm* — Holtz, Holtz, Goodman & Chick PC

(57) ABSTRACT

Forward and backward movement of a wire guide member in an axial direction of the wire guide member is restricted, by the wire guide member abuts on a distal end portion holding member and a proximal end portion holding member. The wire guide member is held by an intermediate holding member, the distal end portion holding member, and the proximal end portion holding member to allow insertion and forward and backward movement in the intermediate holding member, the distal end portion holding member, and the proximal end portion holding member. The wire guide member has elasticity.

4 Claims, 12 Drawing Sheets

(56) References Cited

U.S. PATENT DOCUMENTS

| | | | |
|---|---|---|---|
| 8,591,404 B2 * | 11/2013 | Yamazaki | 600/146 |
| 2002/0017515 A1 | 2/2002 | Obata et al. | |
| 2007/0043261 A1 * | 2/2007 | Watanabe et al. | 600/144 |
| 2007/0299311 A1 * | 12/2007 | Sato et al. | 600/146 |
| 2009/0240110 A1 * | 9/2009 | Miyawaki et al. | 600/149 |

FOREIGN PATENT DOCUMENTS

| | | |
|---|---|---|
| JP | 4-801 U | 1/1992 |
| JP | 2002-191550 A | 7/2002 |
| JP | 2005-237608 A | 9/2005 |
| JP | 2009-78012 A | 4/2009 |
| JP | 2009-106697 A | 5/2009 |

\* cited by examiner

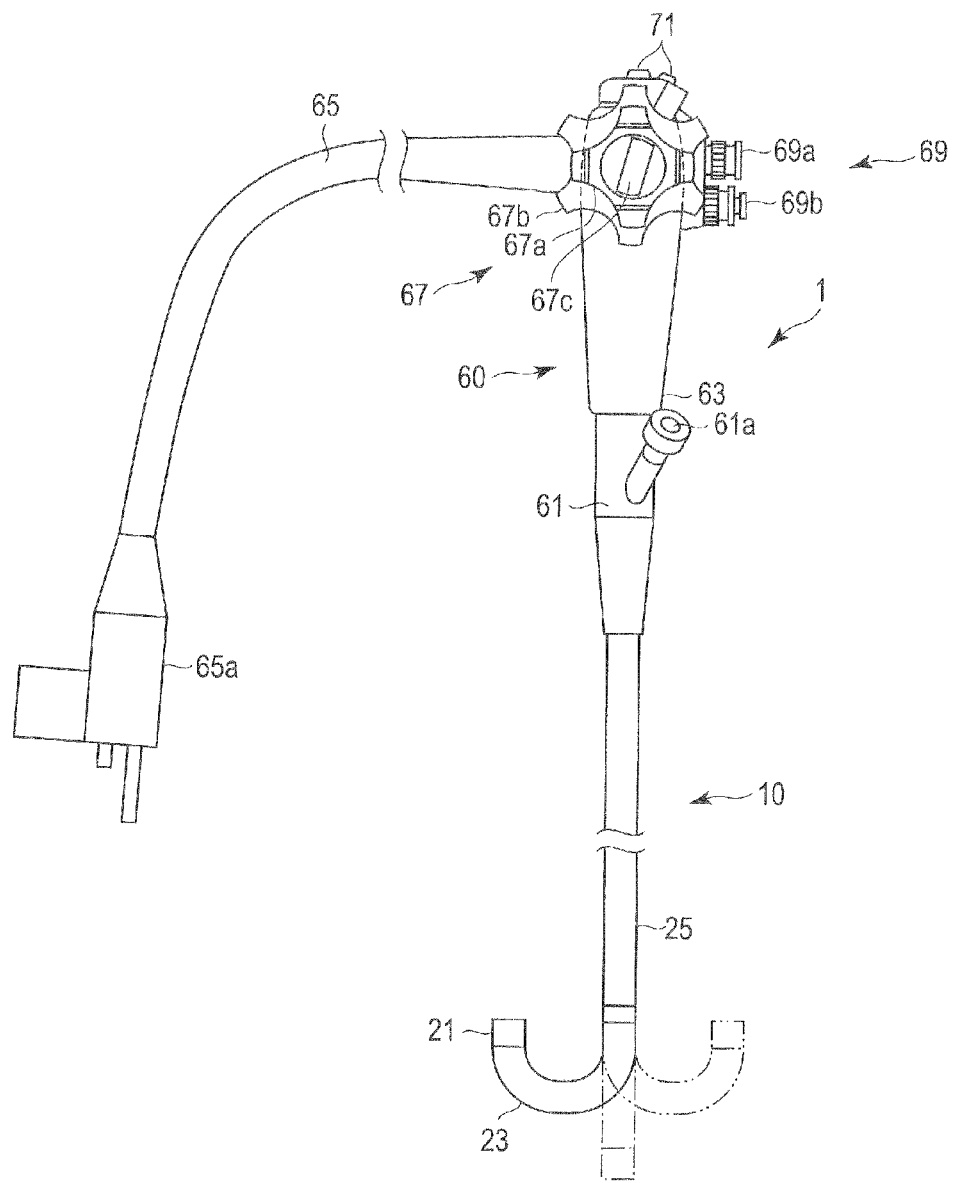
F I G. 1

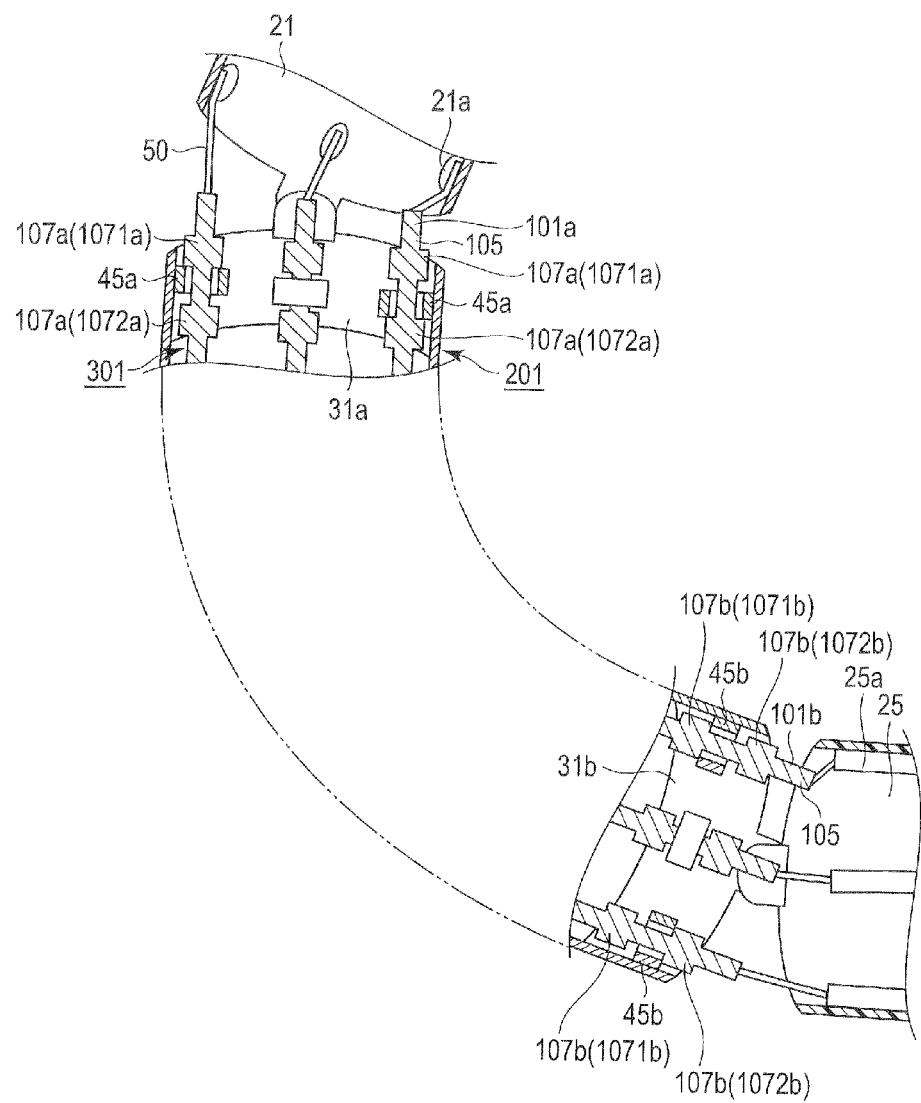
F I G. 7C

WIRE GUIDE MEMBER

CROSS REFERENCE TO RELATED APPLICATIONS

This application is a Continuation Application of PCT Application No. PCT/JP2011/065,800, filed Jul. 11, 2011 and based upon and claiming the benefit of priority from prior Japanese Patent Application No. 2010-186241, filed Aug. 23, 2010, the entire contents of all of which are incorporated herein by reference.

BACKGROUND OF THE INVENTION

1. Field of the Invention

The present invention relates to a wire guide member that guides an operation wire arranged in a bending portion of an insertion unit.

2. Description of the Related Art

In general, a bending portion of an endoscope is configured by coupling node rings with each other to allow their revolving motion. The bending portion is operated by an operation wire, and this operation wire is inserted into the node rings. Further, each node ring has a holding member (a wire receiving member) that holds the operation wire. This holding member is arranged to improve operability in a pulling operation of the operation wire. The holding member is a cylindrical member welded on, for example, an inner peripheral surface of the node ring. Alternatively, the holding member is formed by cutting and bending the inner peripheral surface of the node ring based on press working.

Further, a wire guide member is inserted in each node ring. The wire guide member is inserted in the holding member (the wire receiving member). At this time, the operation wire is inserted in this wire guide member. The wire guide member avoids interference of the operation wire and any other constituent member and guides the operation wire. The above-described holding member holds the operation wire through the wire guide member.

For example, in Jpn. UM Appln. KOKOKU Publication No. 58-46801, a cylindrical wire insertion hole is arranged in a joint shaft and functions as a holding member (the wire receiving member) that can be linearly or smoothly formed.

Furthermore, Jpn. Pat. Appln, KOKAI Publication No. 2005-237608 discloses a bending portion of an endoscope that compression force of a coil spring is used as resistance so that the bending portion can start bending from a distal end portion thereof. Moreover, Jpn. Pat. Appln. KOKAI Publication No. 2005-237608 discloses the bending portion of the endoscope that a compression rate of the coil spring involved by a bending operation is reduced to prevent a bending operation from becoming heavy and durability of the operation wire is improved.

Additionally, Jpn. Pat. Appln. KOKAI Publication No. 2009-78012 discloses an endoscope that a bending portion can be bent from a distal end side thereof and the bent bending portion can be readily restored.

BRIEF SUMMARY OF THE INVENTION

According to an aspect of embodiments, a wire guide member which is held by a holding member to allow insertion and forward and backward movement in the holding member along an axial direction of the holding member, in which an operation wire that bends a bending portion is inserted, and which guides the operation wire, the holding member being arranged in node rings which are adjacent to each other and coupled to allow their revolving motion to form the bending portion, wherein, by the wire guide member abuts on a distal end portion holding member which is the holding member arranged in a distal end portion node ring which is the node ring at a distal end portion of the bending portion and also abuts on a proximal end portion holding member which is the holding member arranged in a proximal end portion node ring which is the node ring at a proximal end portion of the bending portion, forward and backward movement of the wire guide member in the axial direction is restricted, the wire guide member is held by an intermediate holding member, which is the holding member arranged in an intermediate node ring that is at least one node ring between the distal end portion node ring and the proximal end portion node ring, the distal end portion holding member, and the proximal end portion holding member to allow insertion and forward and backward movement in the intermediate holding member, the distal end portion holding member, and the proximal end portion holding member along the axial direction of the holding member, and the wire guide member has elasticity.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view of an endoscope according to the present invention;

FIG. 7C is a view showing a state of the wire guide member when the bending portion bends;

DETAILED DESCRIPTION OF THE INVENTION

Embodiments according to the present invention will now be described hereinafter with reference to the accompanying drawings.

A first embodiment will be explained with reference to FIG. 1, FIG. 2, FIG. 3A, FIG. 3B, FIG. 4A, FIG. 4B, and FIG. 5.

Figure 2:
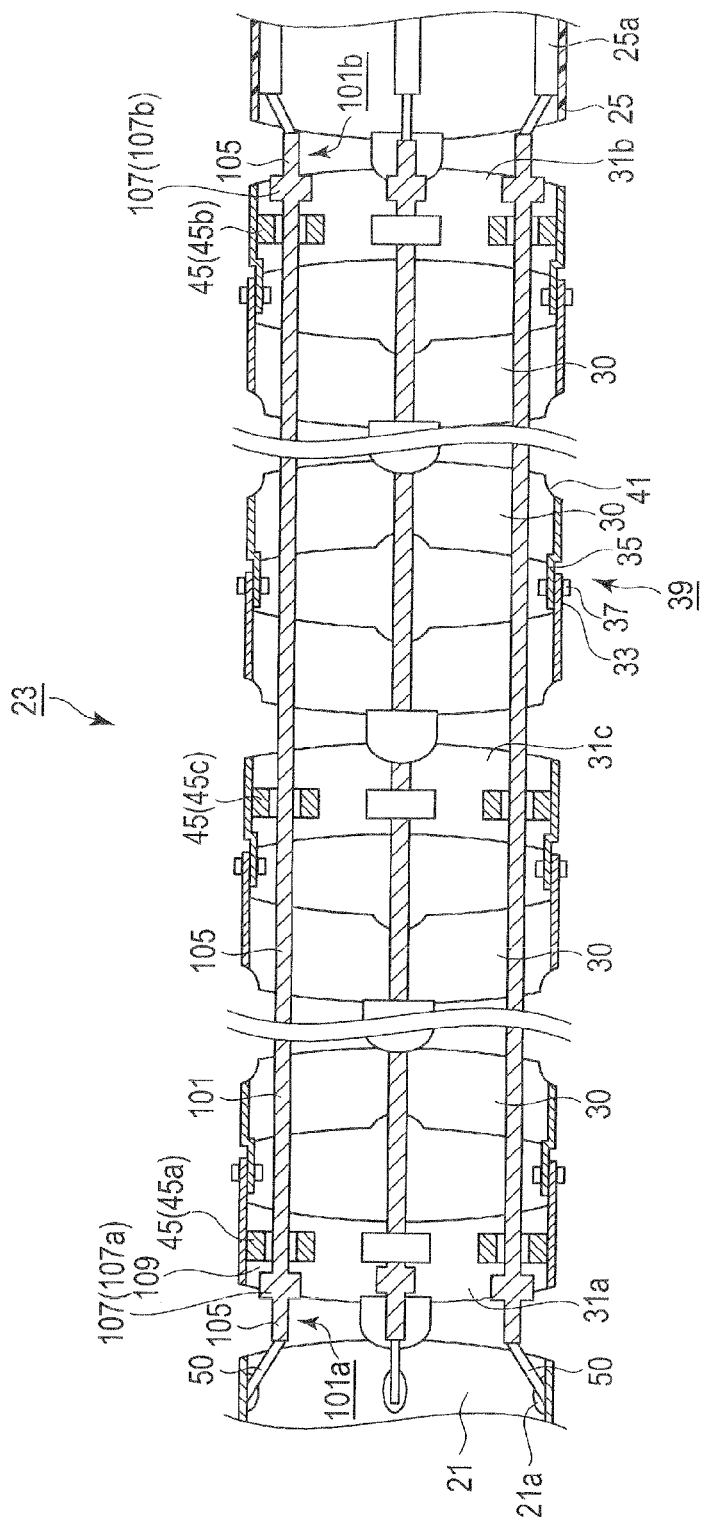
FIG. 2 is a view showing a configuration of a bending portion.

It should be noted that, like omission of built-in features such as a suction channel in FIG. 2, some of the constituent members are omitted in some of drawings for simplification of diagrammatic representation.

Further, in this embodiment, a longitudinal direction of an insertion unit 10, a longitudinal direction of a bending portion 23, an axial direction of a wire guide member 101, an axial direction of a node ring 30, and an axial direction of a holding member 45 are the same direction.

As shown in FIG. 1, an endoscope 1 has an elongated insertion unit 10 which is inserted into, for example, a patient's body cavity and an operation unit 60 which is coupled with a proximal end portion of the insertion unit 10 and operates the endoscope 1.

The insertion unit 10 has a distal end hard portion 21, a bending portion 23, and a flexible tube portion 25 from a distal end portion side of the insertion unit 10 toward the proximal end portion side of the insertion unit 10. A proximal end portion of the distal end hard portion 21 is coupled with a distal end portion of the bending portion 23, and a proximal end portico of the bending portion 23 is coupled with a distal end portion of the flexible tube portion 25.

The distal end hard portion 21 is the distal end portion of the insertion unit 10, and the distal end hard portion 21 is hard.

The flexible tube portion 25 has desired flexibility and bends by external force. The flexible tube portion 25 is a tubular member that is extended from a later-described main body portion 61 in the operation unit 60.

The bending portion 23 will be described later.

The operation unit 60 has a main body portion 61 from which the flexible tube portion 25 is extended, a grip portion 63 that is coupled with a proximal end portion of the main body unit 61 and gripped by an operator who manipulates the endoscope 1, and a universal cord 65 connected with the grip portion 63.

The main body portion 61 has a surgical instrument insertion opening 61a. The surgical instrument insertion opening 61a is coupled with a proximal end portion of a non-illustrated surgical instrument insertion channel. The surgical instrument insertion channel is arranged from the flexible tube portion 25 to the distal end hard portion 21 in the insertion unit 10. The surgical instrument insertion opening 61a is an insertion opening through which a non-illustrated endoscope surgical instrument is inserted into the surgical instrument insertion channel. The non-illustrated endoscopic surgical instrument is inserted into the surgical instrument insertion channel from the surgical instrument insertion opening 61a and pushed into the distal end hard portion 21 side. Furthermore, the endoscopic surgical instrument is made to protrude from a non-illustrated distal end opening portion of the surgical instrument insertion channel arranged in the distal end hard portion 21.

The grip portion 63 has a bending operating portion 67 which bends the bending portion 23. The bending operating portion 67 has a left-right bending operation knob 67a that bonds the bending portion 23 in left and right directions, an up-down bending operation knob 67b that bends the bending portion 23 in upward and downward directions, and a fixing knob 67c that fixes a position of the bent bending portion 23.

The left-right bending operation knob 67a is connected to a non-illustrated bending operation mechanism for left and right directions which is driven by the left-right bending operation knob 67a. Furthermore, the up-down bending operation knob 67b is connected to a non-illustrated bending operation mechanism for upward and downward directions which is driven by the up-down bending operation knob 67b. The bending operation mechanism for the upward and downward directions and the bending operation mechanism for the left and right directions are arranged in the operation unit 60.

The bending operation mechanism for the left and right directions is connected with a proximal end portion of an operation wire 50 which is inserted in the flexible tube portion 25 and the bending portion 23. For example, a distal end portion of this operation wire 50 is connected to the distal end hard portion 21 through, for example, a connection member 21a such as solder as shown in FIG. 2.

Moreover, the bending operation mechanism for the upward and downward directions is connected to a proximal end portion of an operation wire 50 which is inserted in the flexible tube portion 25 and the bending portion 23. The operation wire 50 connected with the bending operation mechanism for the upward and downward directions is different from the operation wire 50 connected with the bending operation mechanism for the left and right directions. For example, a distal end portion of the operation wire 50 connected with the bending operation mechanism for the upward and downward directions is connected with the distal end hard portion 21 through, for example, a connection member 21a such as solder.

The left-right bending operation knob 67a bends the bending portion 23 in the left and right directions via the bending operation mechanism for the left and right directions and the operation wire 50. Additionally, the up-down bending operation knob 67b bends the bending portion 23 in the upward and downward directions via the bending operation mechanism for the upward and downward directions and the operation wire 50.

Further, the grip portion 63 has a switch portion 69 that is manually operated by an operator when the grip portion 63 is gripped by the operator. The switch portion 69 has a suction switch 69a and an air supply/water supply switch 69b. The suction switch 69a is operated when the endoscope 1 suctions mucus, a fluid, or the like from a non-illustrated suction opening portion arranged in the distal end hard portion 21 via a non-illustrated suction channel. The air supply/water supply switch 69b is operated when a fluid is subjected to air supply/water supply from a non-illustrated air supply/water supply channel in order to assure an observation viewing filed of a non-illustrated imaging unit arranged in the distal end hard portion 21. The fluid includes water, a gas, and others.

For example, the operation wire 50, the suction channel, the air supply/water supply channel, a cable in the imaging unit, a later-described wire guide member 101 are built-in features included in the insertion unit 10 (the distal end hard portion 21, the bending portion 23, and the flexible tube portion 25). It should be noted that, as shown in FIG. 2, in the flexible tube portion 25, the operation wire 50 is inserted in a wire guide member 25a arranged in the flexible tube portion 25. The wire guide member 25a avoids interference between the operation wire 50 and built-in features except for the operation wire 50 in the flexible tube portion 25.

Further, the grip portion 63 has various kinds of buttons 71 for endoscopic photography.

The universal cord 65 has a connecting portion 65a that is connected to a non-illustrated video processor or a light source device.

The bending portion 23 will now be described with reference to FIG. 2.

Each operation wire 50 inserted in the flexible tube portion 25 is inserted in the bending portion 23. When each operation wire 50 is pulled by the bending operating portion 67, the bending portion 23 bends in a desired direction, for example, an upward, downward, left, or right direction. When the bending portion 23 bends, a position and a direction of the distal end hard portion 21 vary, en observation target is illuminated with illumination light, and the observation target is captured in an observation viewing field.

As shown in FIG. 2, the bending portion 23 is constituted by aligning substantially cylindrical (annular) node rings 30 along a longitudinal direction of the insertion unit 10. The node rings 30 which are adjacent to each other (placed at front and rear positions along the longitudinal direction of the insertion unit 10) are coupled with each other to allow their revolving motion by a later-described coupling portion 39. When the node rings 30 are coupled with each other to allow their revolving motion in this manner, the bendable (revolvable) bending portion 23 is formed as described above.

The node ring 30 will now be described with reference to FIG. 3A and FIG. 3B.

Each node ring 30 has a substantially cylindrical shape. Such node rings 30 are aligned along the longitudinal direction of the insertion unit 10 as shown in FIG. 2. The node rings 30 which are adjacent to each other are coupled with each other to allow their revolving motion by the coupling portion 39 in order to form the bending portion 23 as described above.

Each node ring 30 is made of a hard material such as a metal. The node ring 30 is molded using, for example, a sheet metal press product or a casting product.

The node ring 30 has two protruding pieces (front hinge bases) 33 on a distal end portion side (the left side in each of FIG. 3A and FIG. 3B) of the node ring 30. Each protruding piece 33 is a portion formed by planarly protruding a part of the node ring 30 toward the front side (the distal end portion side of the bending portion 23). Further, the protruding piece 33 has a through hole 33a that is pierced in the protruding piece 33 in a direction orthogonal to an axial direction of the node ring 30. The two protruding pieces 33 are arranged to be substantially 180° away from each other in the circumferential direction.

Furthermore, each node ring 30 has two protruding pieces (rear hinge bases) 35 on a rear end portion side (the right side in each of FIG. 3A and FIG. 33) of the node ring 30. The protruding piece 35 is a portion formed by planarly protruding a part of the node ring 30 toward the rear side (the proximal end portion side of the bending portion 23). Moreover, the protruding piece 35 has a step substantially corresponding to a board thickness of the protruding piece 33. Additionally, in the protruding piece 35 is formed a through hole 35a that is pierced in the protruding piece 33 in the direction orthogonal to the axial direction of the node ring 30. The two protruding pieces 35 are arranged to be substantially 180° away from each other in the circumferential direction. The axial direction of the through hole 35a is orthogonal to the axial direction of the through hole 33a?.

The two protruding pieces 33a on the front side and the two protruding pieces 35 on the rear side are arranged at positions that are substantially 90° away from each other in the circumferential direction.

As shown in FIG. 2, in each protruding piece 35 of the node ring 30 on the flexible tube portion 25 side and each protruding piece 33 of the node ring 30 on the distal end hard portion 21 side, a rivet 37 which is a revolving member (a pivot) is inserted into the through holes 33a and 35a. As a result, the node ring 30 on the flexible tube portion 25 side is coupled with the node ring 30 on the distal end hard portion 21 side through the rivet 37, and they are pivotally supported to allow their revolving motion about the rivet 37. In this manner, a spindle portion using the rivet 37 as a revolving spindle is formed between the protruding piece 33 and the protruding piece 35.

Furthermore, in other words, the protruding piece 33, the protruding piece 35, and the rivet 37 function as the coupling portion 39 that couples the node ring 30 on the flexible tube portion 25 side with the node ring 30 on the distal end hard portion 21 side.

It should be noted that, when the node rings 30 are coupled with each other through the rivet 37, each protruding piece 33 of the node ring 30 on the flexible tube portion 25 side is laminated on each protruding piece 35 of the node ring 30 on the distal end hard portion 21 side.

In the bending portion 23 according to this embodiment, the rivets 37 serving as the revolving members that couple the node rings 30 with each other are alternately arranged to be substantially 90° shifted on the front and rear sides of each node ring 30. As a result, the bending portion 23 is configured to bend in four directions, namely, the upward, downward, left, and right directions.

Moreover, each node ring 30 has notch portions 41.

Each notch portion 41 is arranged on the same straight line as each protruding piece 35 in the axial direction of the node ring 30, arranged on the distal end portion side (the left side in each of FIG. 3A and FIG. 3B, the distal end hard portion 21 side) of the node ring 30 away from the protruding piece 35, and arranged to be substantially 90° shifted with respect to the protruding piece 33 in the circumferential direction. Each notch portion 41 is opened toward the distal end hard portion 21.

Additionally, each notch portion 41 is arranged on the same straight line as each protruding piece 33 in the axial direction of the node ring 30, arranged on the rear end portion side (the right side in each of FIG. 3A and FIG. 3B, the flexible tube portion 25 side) of the node ring 30 away from the protruding piece 33, and arranged to be substantially 90° shifted with respect to the protruding piece 35 in the circumferential direction. Each notch portion 41 is opened toward the flexible tube portion 25 side.

Each notch portion 41 is arranged to prevent the wire guide member 10 from coming into contact with the node ring 30 and becoming worn when the bending portion 23 bends as shown in later-described FIG. 5.

Figure 3A:
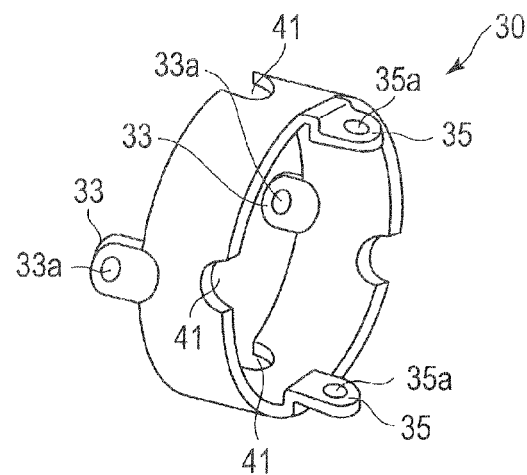
FIG. 3A is a perspective view of a node ring.
Figure 3B:
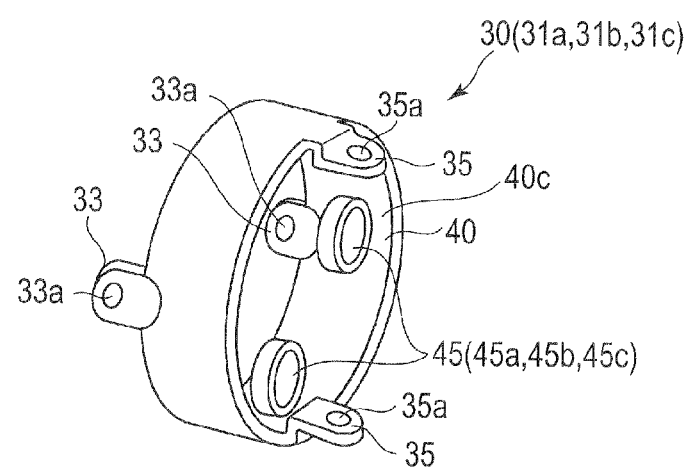
FIG. 3B is a perspective view of a distal end portion node ring, a proximal end portion node ring, and an intermediate node ring.

It should be noted that, in this embodiment, as shown in FIG. 3B, the node ring 30 arranged at the distal end portion of the bending portion 23 is determined as a distal end portion node ring (which will be referred to as node ring 31a hereinafter), and the node ring 30 arranged at the proximal end portion of the bending portion 23 is determined as a proximal end portion node ring (which will be referred to as node ring 31b hereinafter). Further, at least one node ring 30 arranged between node ring 31a and node ring 31b is determined as an intermediate node ring (which will be referred to as node ring 31c). Node ring 31c represents at least one node ring 30 excluding node ring 31a and node ring 31b.

As shown in FIG. 2, node ring 31a is coupled with the distal end hard portion 21, and node ring 31b is coupled with the flexible tube portion 25. Furthermore, node ring 31c is arranged at, for example, an intermediate part of the bending portion 23 in the longitudinal direction of the bending portion 23.

As shown in FIG. 3A and FIG. 3B, a configuration of each of node rings 31a, 31b, and 31c is substantially equal to the node ring 30. However, the notch portions 41 are not arranged in each of node rings 31a, 31b, and 31c. Moreover, as shown in FIG. 3B, each of node rings 31a, 31b, and 31c has the holding members 45 that hold the later-described wire guide members 101 on en inner peripheral surface 40 of each of node rings 31a, 31b, and 31c. The holding members 45 of node rings 31a, 31b, and 31c are determined as holding members 45a, 45b, and 45c, respectively. Holding members 45a are distal end portion holding members arranged at the distal end portion of the bending portion 23. Additionally, holding members 45b are proximal, end portion holding members arranged at the proximal end portion of the bending portion 23. Further, holding members 45c are intermediate holding members. As described above, each of node rings 31a, 31b, and 31c has the holding members 45 that hold the later-described wire guide members 101.

Each holding member 45 is a receiving member that receives the wire guide member 101. It should be noted that the operation wire 50 is inserted in the wire guide member 101. Therefore, each holding member 45 is a wire receiving member that holds the operation wire 50 through the wire guide member 101 and receives the operation wire 50 via the wire guide member 101.

Each holding member 45 is made of a hard material, for example, a metal. The holding member 45 has, for example, a cylindrical shape. The wire guide member 101 is inserted and moves forward and backward in the holding member 45 in the axial direction of the holding member 45. The holding member 45 is fixed on the inner peripheral surface 40 of each of node rings 31a, 31b, and 31c by, for example, welding. Each holding member 45 is arranged on the same straight line of each of the protruding pieces 33 and 35 in the longitudinal direction of the bending portion 23. Therefore, in each of node rings 31a, 31b, and 31c, the four holding members 45 are arranged to be 90° apart in the circumferential direction. Each holding member 45 arranged in each of node rings 31a, 31b, and 31c is arranged on the same straight line in the longitudinal direction of the bending portion 23.

The wire guide member 101 will now be described with reference to FIG. 2, FIG. 4A, and FIG. 4B.

The wire guide member 101 is a tubular member having elasticity. The wire guide member 101 is held by the holding member 45 so that the wire guide member 101 can be inserted and moved forward and backward in the holding member 45 along the axial direction of the holding member 45. The operation wire 50 is inserted in this wire guide member 101 so that the operation wire 50 can freely move forward and backward along the axial direction of the wire guide member 101. Such a wire guide member 101 is a wire insertion member in which the operation wire 50 is inserted. Further, the wire guide member 101 guides the operation wire 50 from the proximal end portion the bending portion 23 to the distal end portion of the bending portion 23 in the bending portion 23. Furthermore, the wire guide member 101 protects the operation wire 50 against built-in features except for the operation wire 50. Such a wire guide member 101, for example, a coil spring wound around the operation wire 50.

As shown in FIG. 2, the forward and backward movement of the wire guide member 101 in the axial direction of the wire guide member 101 is restricted by the wire guide member 101 abuts on holding member 45a and holding member 45b.

In detail, the wire guide member 101 has a distal end portion 101a held by the holding member 15a and a proximal end portion 101b held by the holding member 45b. On the distal end portion 101a side and the proximal end portion 101b side, the forward and backward movement of the wire guide member 101 in the axial direction thereof is restricted.

Figure 4A:
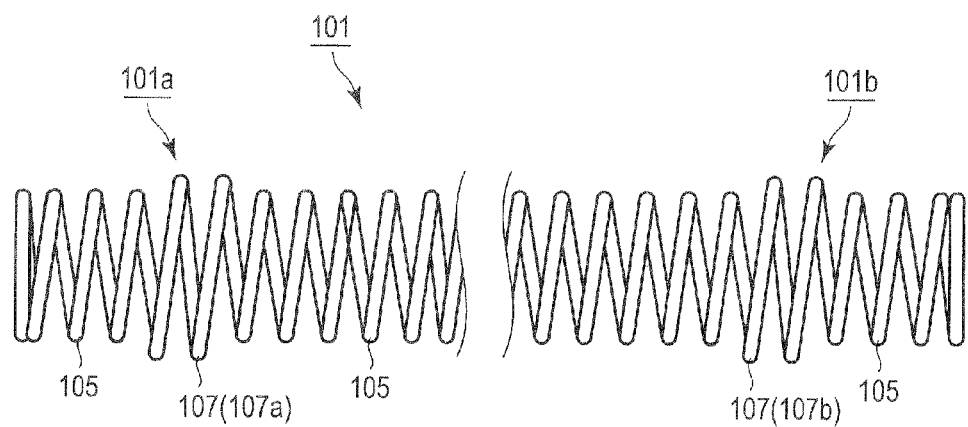
FIG. 4A is a side elevation of a wire guide member in a first embodiment.

In more detail, as shown in FIG. 2 and FIG. 4A, the wire guide member 101 has a small-diameter portion 105 which is held by the holding member 45 so that the wire guide member 101 can be inserted and move forward and backward in the holding member 45 along the axial direction of the holding member 45 and a large-diameter portion 107 which has a cross section with a larger diameter than the small-diameter portion 105, buts on holding member 45a and holding member 45b when the bending portion 23 bends, and restricts the forward and backward movement of the wire guide member 101 along the axial direction of the wire guide member 101.

The small-diameter portion 105 is formed between the distal end portion 101a side and the proximal end portion 101b side. In detail, the small-diameter portion 105 represents the wire guide member 101 excluding the large-diameter portion 107. That is, as shown in FIG. 2, the small-diameter portion 105 represents the wire guide member 101 which is arranged between node ring 31a and node ring 31b in the axial direction, the wire guide member 101 on the distal end portion 101a side than large-diameter portion 107a, and the wire guide member 101 on the proximal end portion. 101b side than large-diameter portion 107b.

Figure 4B:
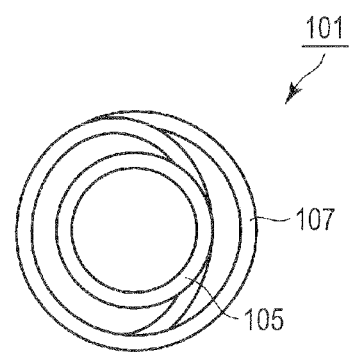
FIG. 4B is a front view of the wire guide member.

As shown in FIG. 4B, the large-diameter portion 107 is also a bulge portion that bulges beyond the small-diameter portion 105 in the radial direction. The large-diameter portion 107 is formed on each of the distal end portion 101a side and the proximal end portion 101b side. That is, the large-diameter portion 107 represents the wire guide member 101 arranged on each of the distal end portion 101a side and the proximal end portion 101b side.

In the following description, the large-diameter portion 107 on the distal end portion 101a side is determined as a large-diameter portion 107a, and the large-diameter portion 107 on the proximal end portion 101b side is determined as a large-diameter portion 107b. Each of large-diameter portions 107a and 107b will now be described.

In this embodiment, large-diameter portion 107a on the distal end portion 101a side is arranged on the distal end portion (the distal end hard portion 21) side of the bending portion 23 than holding member 45a in the axial direction of the wire guide member 101 in such, a manner that large-diameter portion 107a abuts on holding member 45a. Large-diameter portion 107b on the proximal end portion 101b side is arranged on the proximal end portion (the flexible tube portion 25) side of the bending portion 23 than holding member 45b in the axial direction of the wire guide member 101 in such a manner that large-diameter portion 107b abuts on holding member 45b.

Figure 5:
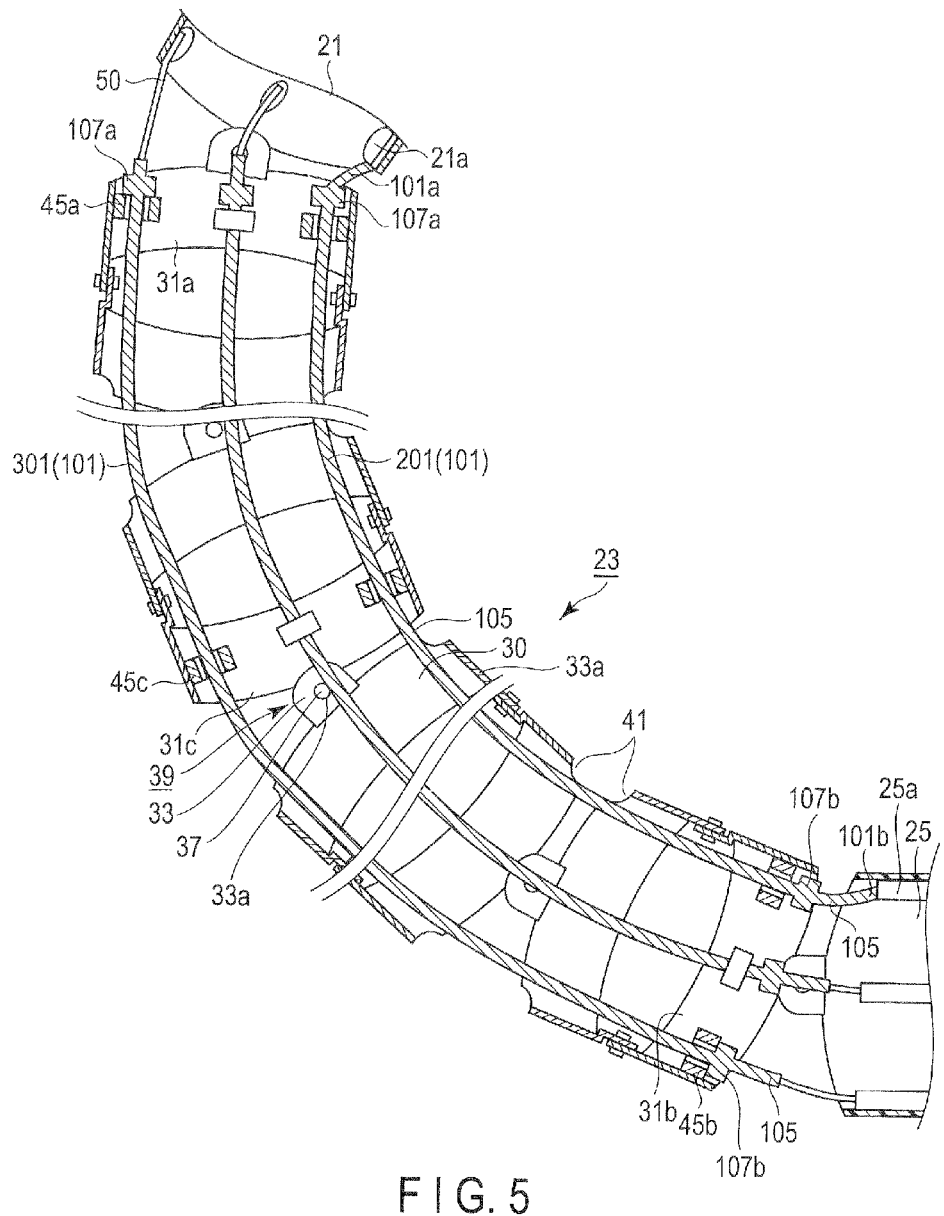
FIG. 5 is a view showing a state of the wire guide member when the bending portion bends.

When the bending operating portion 67 is operated and the bending portion 23 bends, as shown in FIG. 5, the wire guide member 201 arranged on the inner side of the bent bending portion 23 shrinks. In this wire guide member 201, the distal end portion 101a abuts on the connection member 21a, and the proximal end portion 101b abuts on the wire guide member 25a. As a result, the forward and backward movement of the wire guide member 201 in the axial direction thereof is restricted with respect to the bending portion 23.

It should be noted that, in the wire guide member 201 arranged on the inner side of the bending portion 23, large-diameter portion 107a may abut on holding member 45a, and large-diameter portion 107b may abut on holding member 45b. This configuration likewise restricts the forward and backward movement of the wire guide member 201 in the axial direction of the wire guide member 201 with respect to the bending portion 23.

The wire guide member 201 has a length that allows the distal end portion 101a to abut on the connection member 21a and allows the proximal end portion 101b to abut on the wire guide member 25a or allows large-diameter portion 107a to abut on holding member 45a and allows large-diameter portion 107b to abut on holding member 45h when the bending portion 23 and the wire guide member 201 bend in this manner.

Alternatively, when the bending operating portion 67 is operated and the bending portion 23 bends, as shown in FIG. 5, the wire guide member 301 arranged on the outer side of the bent bending portion 23 extends. In this wire guide member 301, large-diameter portion 107a abuts on holding member 45a, and large-diameter portion 107b abuts on holding member 45b. At this time, large-diameter portion 107a restricts the forward and the backward movement of the wire guide member 101 toward the proximal end portion side (the flexible tube portion 25) when the bending portion 23 bends. Further, large-diameter portion 107b restricts the forward and backward movement, of the wire guide member 101 toward the distal end portion side (the distal end hard portion 21) of the bending portion 23 when the bending portion 23 bends. As a result, the forward and backward movement of the wire guide member 101 in the axial direction of the wire guide member 101 is restricted with respect to the bending portion 23. As described above, the large-diameter portion 107 is a restricting portion that restricts the forward and backward movement of the wire guide member 101 in the axial direction of the wire guide member.

It should be noted that the wire guide member 301 has a length that allows the distal end portion 101a to abut on holding member 45a and also allows the proximal end portion 101b to abut on holding member 45b when the bending portion 23 and the wire guide member 310 bend.

It should be noted that, as shown in FIG. 4B, each of the small-diameter portion 105 and the large-diameter portion 107 has, for example, a ring-like cross-sectional shape. Further, as shown in FIG. 4B, the small-diameter portion 105 and the large-diameter portion 107 are similar to each other.

Further, an outside diameter of the small-diameter portion 105 is smaller than an inside diameter of the holding member 45 so that the wire guide member 101 in the small-diameter portion 105 can be inserted and moved forward and backward in the holding member 45 in the axial direction of the holding member 45. Furthermore, in the small-diameter portion 105 arranged on the proximal end portion 101b side than large-diameter portion 107b, an inside diameter of this small-diameter portion 105 is larger than an inside diameter of the wire guide member 25a and smaller than an outside diameter of the wire guide member 25a so that the small-diameter portion 105 can abut on the wire guide member 25a in the flexible tube portion 25.

Moreover, an inside diameter of the large-diameter portion 107 is larger than the outside diameter of the small-diameter portion 105. Additionally, the inside diameter of the large-diameter portion 107 is larger than an inside diameter of each of holding members 45a and 45b so that the large-diameter portion 107 can abut on each of holding members 45a and 45b as described above.

In addition, as shown in FIG. 2, it is preferable for the large-diameter portion 107 to be away from each of holding members 45a and 45b so that the large-diameter portion 107 does not abut on each of holding members 45a and 45b and a gap 109 is formed between the large-diameter portion 107 and each of holding members 45a and 45b when the bending portion 23 is linearly arranged and the linear wire guide member 101 is held in each holding member 45.

As described above, the wire guide member 101 has a length that enables the gap 109 to be formed between the large-diameter portion 107 and each of holding members 45a and 45b and allows the large-diameter portion 107 to be away from each of holding members 45a and 45b by a desired distance when the bending portion 23 and the wire guide member 101 are linear.

It should be noted that, in this embodiment, as shown in FIG. 2, the small-diameter portion 105 is formed on the distal end portion 101a side than large diameter portion 107a, and the small-diameter portion 105 is also formed on the proximal end portion 101b side than large-diameter portion 107b, but the present invention is not restricted thereto. For example, the small-diameter portion 105 may be arranged between large-diameter portion 107a and large-diameter portion 107b alone in the axial direction of the wire guide member 101. That is, the wire guide member 101 may have the large-diameter portions 107 at both end portions thereof. In this case, the inside diameter of large-diameter portion 107b is larger than the inside diameter of the wire guide member 25a and smaller than the outside diameter of the wire guide member 25a so that large-diameter portion 107b can abut on the wire guide member 25a in the flexible tube portion 25.

That is, as shown in FIG. 2, the small-diameter portion 105 may be formed on the distal end portion 101a side than large-diameter portion 107a, or large-diameter portion 107a may be formed at the distal end portion 101a. Further, the small-diameter portion 105 may be formed on the proximal end portion 101b side than large-diameter portion 107b, or large-diameter portion 107b may be formed at the proximal end portion 101b.

As described above, in this embodiment, it is good enough for the wire guide member 101 to have one of the small-diameter portion 105 and the large-diameter portion 107 at the distal end portion 101a and have one of the small-diameter portion 105 and the large-diameter portion 107 at the proximal end portion 101b.

An operation method according to this embodiment will now be described with reference to FIG. 5.

It should be noted that the wire guide member 101 arranged on the inner side of the bent bending portion 23 is determined as a wire guide member 201 and the wire guide member 101 arranged on the outer side of the bent bending portion 23 is determined as a wire guide member 301.

The bending operating portion 67 is operated, and the bending portion 23 is bent.

At this time, in the wire guide member 201, the distal end portion 101a abuts on the connection member 21a, and the proximal end portion 101b abuts on the wire guide member 25a. As a result, the forward and backward movement of the wire guide member 201 in the axial direction of the wire guide member 201 is restricted with respect to the bending portion 23, and a change in position of the end portion of the wire guide member 201 (each of the distal end portion 101a and the proximal end portion 101b) in the axial direction is suppressed.

Furthermore, in the wire guide member 301, large-diameter portion 107a abuts on holding member 45a, and large-diameter portion 107b abuts on holding member 45b. As a result, the forward and backward movement of the wire guide member 301 in the axial direction of the wire guide member 301 is restricted with respect to the bending portion 23, and a change in position of the end portion of the wire guide member 301 (each of the distal end portion 101a and the proximal end portion 101b) in the axial direction is suppressed.

Moreover, the wire (guide member 101 has elasticity. Additionally, the wire guide member 101 is held by the holding member 45 so that the wire guide member 101 can be inserted and moved forward and backward in the holding member 45 along the axial direction of the holding member 45. Further, each holding member 45 is arranged in node rings 31a and 31b alone, and it is arranged in at least one node ring 31c alone instead of all the node rings 30. Therefore, when the wire guide member 101 bends, the wire guide member 101 bends in a smooth arc shape.

As a result, when the operation wire 50 is inserted into the bent wire guide member 101, friction of the operation wire 50 and the wire guide member 101 is dispersed and suppressed. Further, the working life of the operation wire 50 is prevented from being considerably reduced, and an increase in real stance when the operation wire 50 is pulled is avoided, and operability of the operation wire 50 is improved.

Furthermore, the wire guide member 101 bends in the smooth arc shape, and each holding member 45 is arranged in node rings 31a and 31b and at least one node ring 30c. Therefore, contact of the wire guide member 101 and the holding member 45 is suppressed to the minimum level, and abrasion of the wire guide member 101 caused by contact with the holding member 45 is suppressed.

It should be noted that the operation wire 50 is guided by the wire guide member 101, and hence the operation wire 50 does not come into contact with the holding member 45. Therefore, abrasion of the operation wire 50 caused by contact with the holding member 45 is suppressed.

Moreover, since arranging each holding member 45 in at least the three node rings 31a, 31b, and 31c can suffice, the trouble of processing and assembling each holding member 45 which is a minute component can be saved, and the endoscope 1 becomes inexpensive.

Further, when the bending portion 23 bends, as shown in FIG. 5, each notch portion 41 enables preventing the wire guide member 101 from abutting on the edge of the node ring 30, and hence friction is dispersed. Therefore, local abrasion of the wire guide member 101 caused by contact with the node ring 30 can be avoided.

As described, above, in this embodiment, the bent wire guide member 101 which is particularly the large-diameter portion 107 abuts on each of holding members 45a and 45b, and the forward and backward movement of the wire guide member 101 in the axial direction of the wire guide member 101 is restricted. Furthermore, in this embodiment, each holding member 45 holds the wire guide member 101 in such a manner that the wire guide member 101 can be inserted and moved backward and forward in each holding member 45 along the axial direction of the holding member 45.

As a result, in this embodiment, a change in position of the end portion of the wire guide member 101 (each of the distal end portion 101a and the proximal end portion 101b) in the axial direction can be suppressed.

Additionally, in this embodiment, the wire guide member 101 has elasticity. As a result, in this embodiment, the wire guide member 101 can be bent in the smooth arc shape, the friction of the operation wire 50 and the wire guide member 101 can be dispersed, a considerable reduction in the working life of the operation wire 50 can be avoided, and the operability of the operation wire 50 can be improved.

Further, in this embodiment, since the wire guide member 101 bends in the smooth arc shape and each holding member 45 is arranged in node rings 31a and 31b and at least one node ring 31c alone, the contact of the wire guide member 101 and the holding member 45 can be suppressed to the minimum level, and the abrasion of the wire guide member 101 caused by the contact with the holding member 45 can be avoided.

Furthermore, in this embodiment, the wire guide member 101 can avoid the contact of the operation wire 50 and the holding member 45, and the abrasion of the operation wire 50 caused by the contact with the holding member 45 can be prevented.

Moreover, in this embodiment, since arranging each holding member 45 in node rings 31a, 31b, and 31c alone can suffice, the trouble of processing and assembling each holding member 45 which is a minute component can be saved, and hence the endoscope 1 becomes inexpensive.

Additionally, in this embodiment, in the bent wire guide member 101, the distal end portion 101a is allowed to abut on the connection member 21a, the proximal end portion 101b is allowed to abut on the wire guide member 25a, and the forward and backward movement of the wire guide member 101 in the axial direction of the wire guide member 101 is restricted. As a result, in this embodiment, a change in position of the end portion of the wire guide member 101 (each of the distal end portion 101a and the proximal end portion 101b) in the axial direction can be suppressed.

Further, in this embodiment, when the wire guide member 101 bends, the small-diameter portion 105 enables the wire guide member 101 to be inserted and moved forward and backward in the holding member 45 along the axial direction of holding member 45. Furthermore, in this embodiment, the large-diameter portion 107 can restrict the forward and backward movement of the wire guide member along the axial direction, whereby a change in position of the end portion of the wire guide member 101 (each of the distal end portion 101a and the proximal end portion 101b) in the axial direction can be suppressed.

Moreover, in this embodiment, since the small-diameter portion 105 and the large-diameter portion 107 are configured to be similar, the wire guide member 101 can be easily manufactured.

Additionally, in this embodiment, since large-diameter portion 107a is arranged on the distal end portion (the distal end hard portion 21) side of the bending portion 23 than holding member 45a and large-diameter portion 107b is arranged on the proximal-end portion (the flexible tube portion 25) side of the bending portion 23 than holding member 45b, a change in position of the end portion of the wire guide member 101 (each of the distal end portion 101a and the proximal end portion 101b) in the axial direction can be easily suppressed.

Further, in this embodiment, each notch portion 41 can prevent the wire guide member 101 from locally abutting on the node ring 30 when the bending portion 23 bends, and local abrasion of the wire guide member 101 can be avoided.

Figure 6:
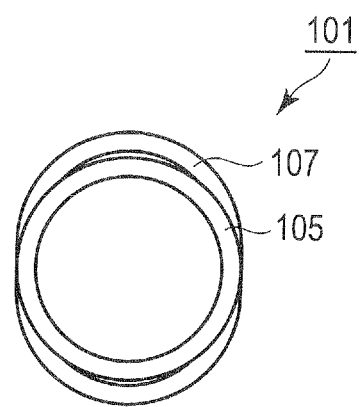
FIG. 6 is a front view of a wire guide member in a first modification.

A first modification of this embodiment will now be described with reference to FIG. 6.

The large-diameter portion 107 in this embodiment bulges in at least one direction of the radial directions of the wire guide member beyond the small-diameter portion 105. For example, when the small-diameter portion 105 has a circular cross section, the large-diameter portion 107 has a larger elliptic cross section than the small-diameter portion 105.

As a result, in this embodiment, the contact of the large-diameter portion 107 and each of holding members 45a and 45h can be suppressed, and the abrasion of the wire guide member 101 caused by the contact with each of holding members 45a and 45b can be alleviated.

Figure 7A:
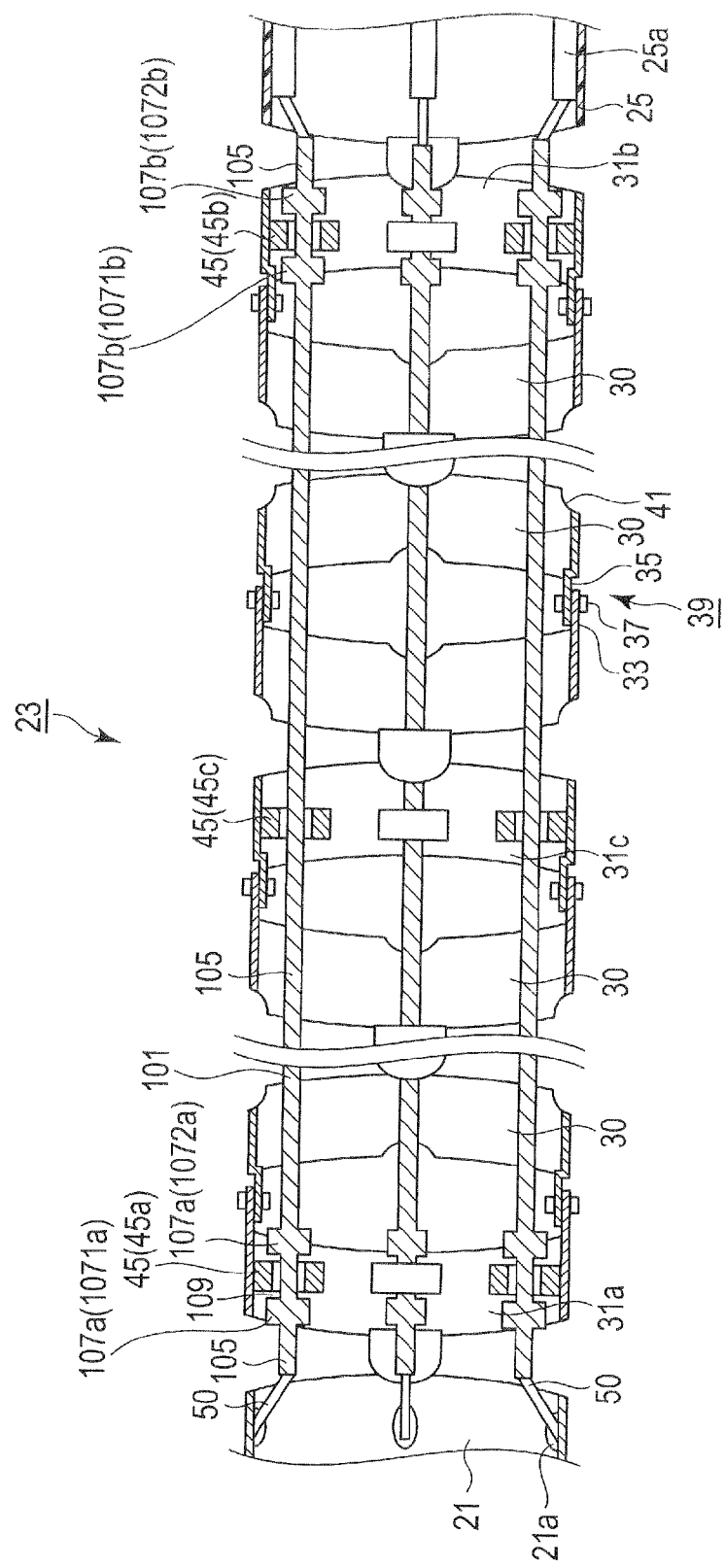
FIG. 7A is a view showing a configuration of a bending portion in a second embodiment.
Figure 7B:
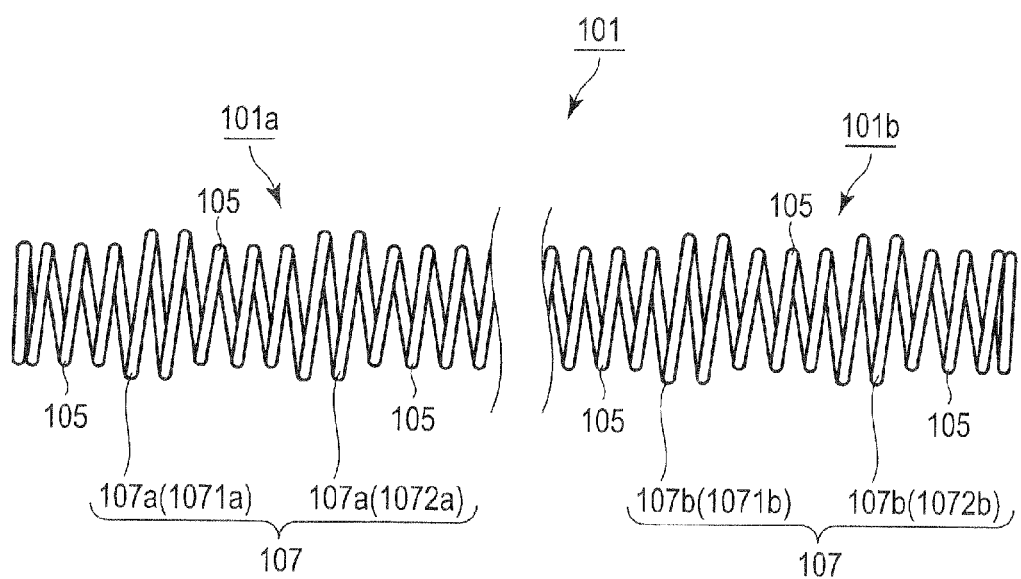
FIG. 7B is a side view of a wire guide member in the second embodiment.

A second embodiment according to the present invention will now be described with reference to FIG. 7A, FIG. 7B, and FIG. 7G.

On a distal end portion 101a side, in order to restrict movement of a wire guide member 101 to a distal end portion side (a distal end hard portion 21 side) and a proximal end portion side (a flexible tube portion 25 side) of a bending portion 23 when the bending portion 23 bends, large-diameter portions 107a are arranged on front and rear sides of a holding member 45a in such a manner that each large-diameter portion 107a abuts on holding member 45a when the bending portion 23 bends and holding member 45a is sandwiched in the axial direction. In this case, along the axial direction, a length of a small-diameter portion 105 between a large-diameter portion 1071a on the front side and a large-diameter portion 1072a on the rear side is equal to or larger than a length of holding member 45a in the axial direction.

Further, on the proximal end portion 101b side, in order to restrict movement of the wire guide member 101 to the distal end portion side (the distal end hard portion 21 side) and the proximal end portion side (the flexible tube portion 25 side) of the bending portion 23 when the bending portion 23 bends, large-diameter portions 107b are arranged on front and rear sides of a holding member 45b in such a manner that each large-diameter portion 107b abuts on holding member 45b when the bending portion 23 bends and holding member 45b is sandwiched in the axial direction. In this case, along the axial direction, a length of a small-diameter portion 105 between a large-diameter portion 1071b on the front side and a large-diameter portion 1072b on the rear side is equal to or larger than a length of holding member 45b in the axial direction.

As shown in FIG. 7C, when the bending portion 23 bends, in the wire guide member 201, large-diameter portion 1072a abuts on holding member 45a, and largo-diameter portion 1071b abuts on holding member 45b. As a result, the forward and backward movement of the wire guide member 201 along the axial direction of the wire guide member 101 is restricted with respect to the bending portion 23, and a change in position of an end portion of the wire guide member 201 (each of a distal end portion 101a and a proximal end portion 101b) in the axial direction is suppressed.

Furthermore, when the bending portion 23 bends, in the wire guide member 301, large-diameter portion 1071a abuts on holding member 45a, and large-diameter portion 1072b abuts on holding member 45b. As a result, the forward and backward movement of the wire guide member 301 in the axial direction of the wire guide member 101 is restricted with respect to the bending portion 23, and a change in position of the end portion of the wire guide member 301 (each of the distal end portion 101a and the proximal end portion 101b) is suppressed.

As described above, in this embodiment, large-diameter portions 107a are arranged on the front and rear sides of holding member 45a, and large-diameter portions 107b are arranged on the front and rear sides of holding member 45b. As a result, in this embodiment, the forward and backward movement of the wire guide member 101 in the axial direction of the wire guide member 101 can be more firmly restricted, and a change in position of the end portion of the wire guide member 101 (each of the distal end portion 101a and the proximal end portion 101b) in the axial direction can be further firmly suppressed.

Figure 8A:
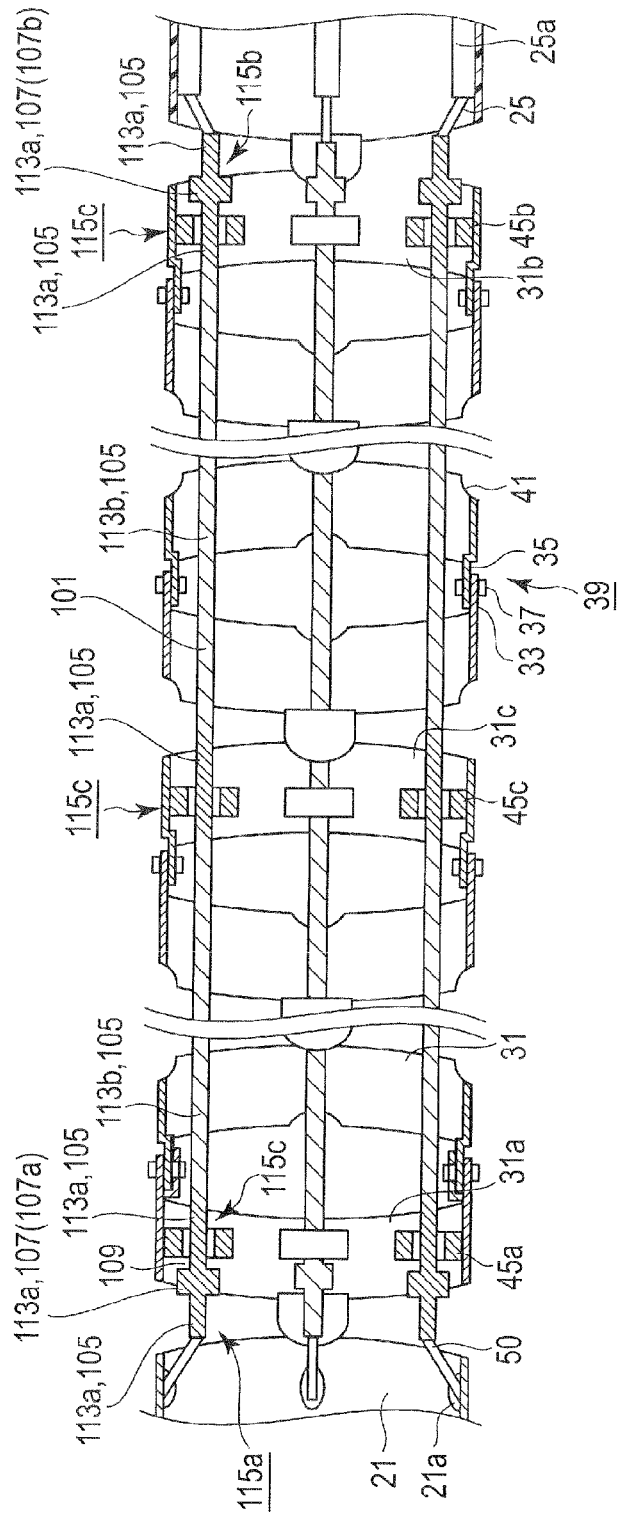
FIG. 8A is a view showing a configuration of a bending portion in a third embodiment.
Figure 8B:
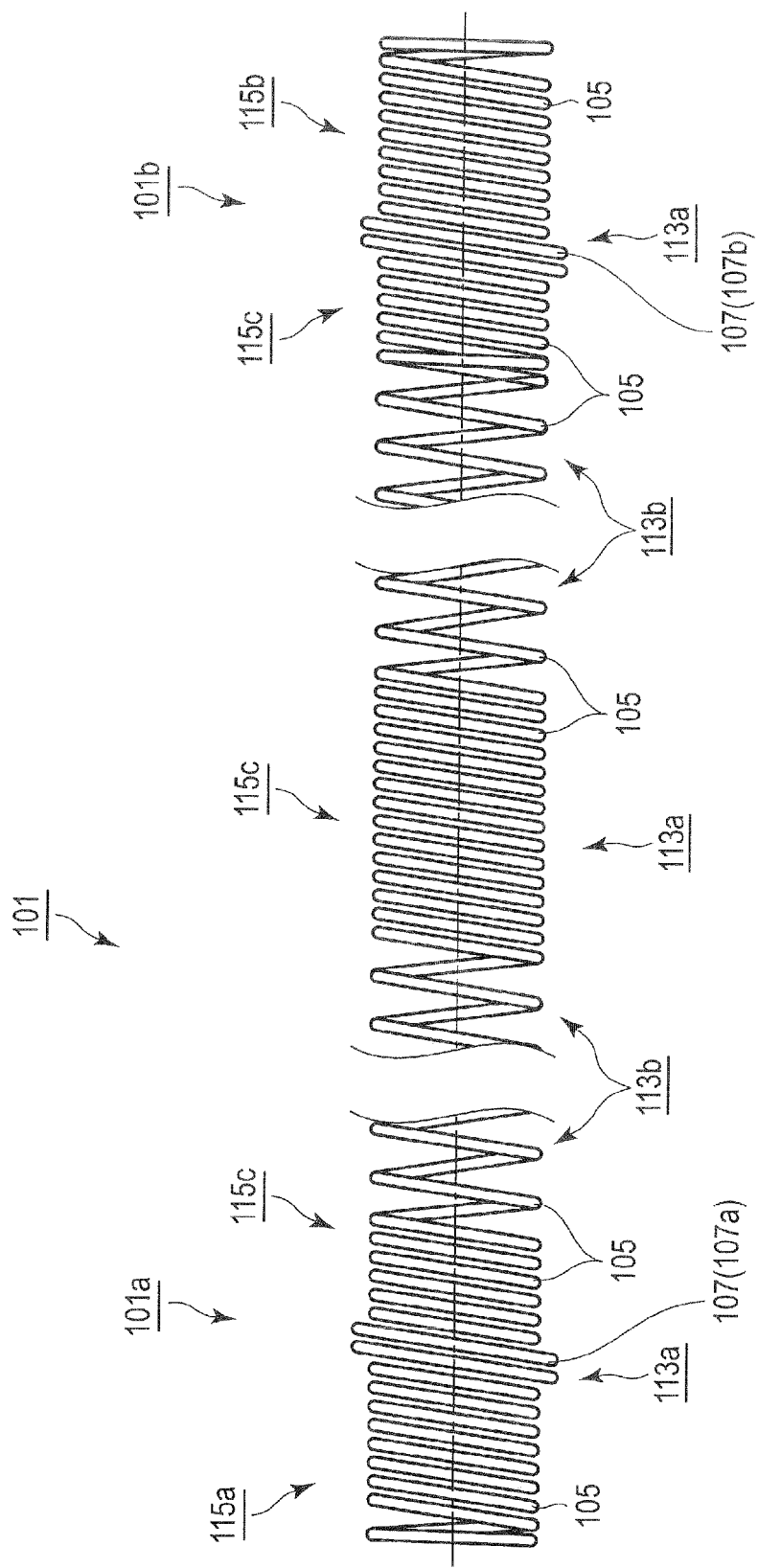
FIG. 8B is a side elevation of a wire guide member in the third embodiment.
Figure 8C:
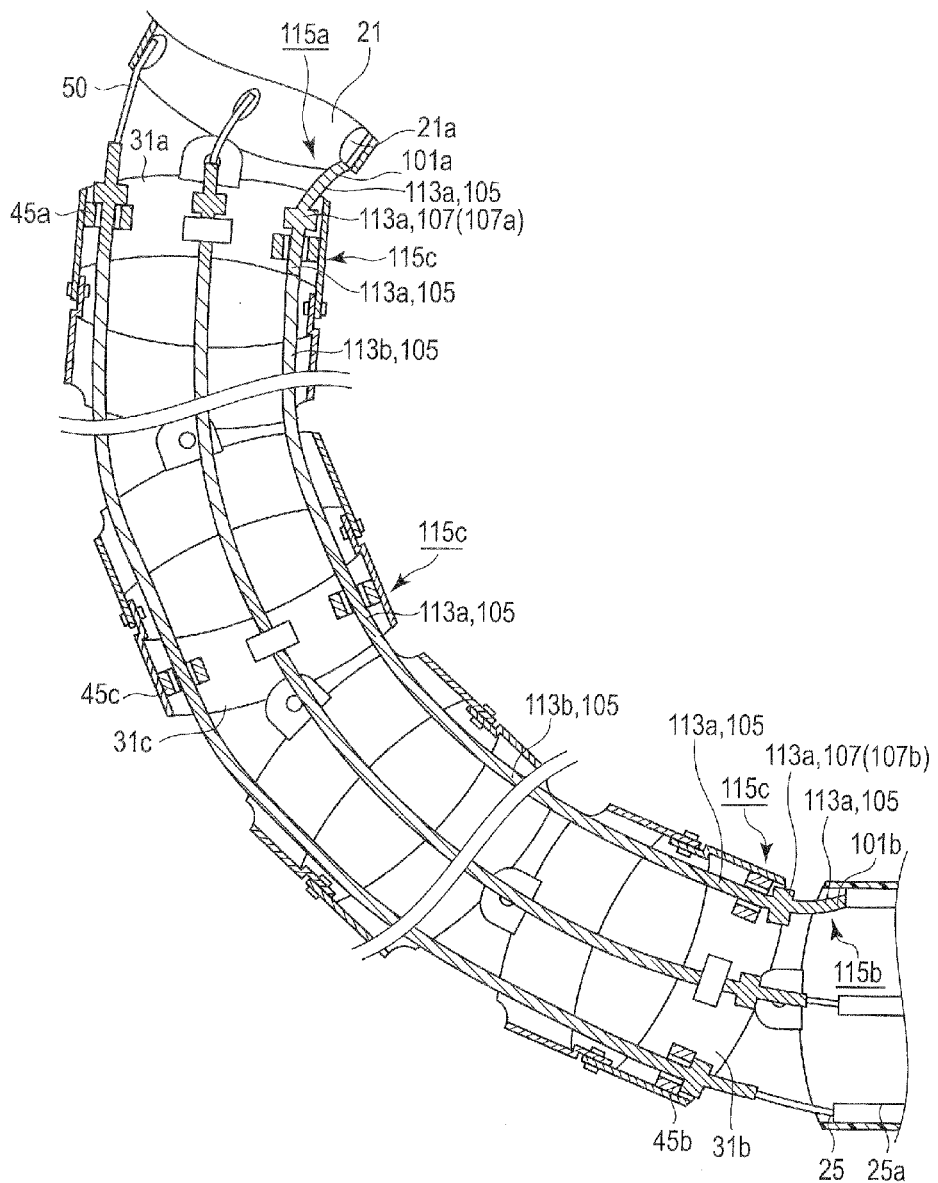
FIG. 8C is a view showing a state of the wire guide member when the bending portion bends.

A third embodiment, according to the present invention will now be described with reference to FIG. 8A, FIG. 8B, and FIG. 8C.

A wire guide member 101 has each close winding portion 113a formed around a portion where a wire guide member 101 including a large-diameter portion 107a is held by a holding member 45 and each loose winding portion 113b which is looser than the close winding portion 113a. The close winding portion 113a and the loose winding portion 113b are, for example, a coil spring.

The close winding portion 113a represents large-diameter portion 107a, a portion 115a on a distal end portion 101a side than large-diameter portion 107a and a holding member 45a, a large diameter portion 107b, a portion 115b on a proximal end portion 101b side than large-diameter portion 107b and a holding member 45b, and a portion 115c held by the holding member 45 when the wire guide member 101 bends or straightens. The loose winding portion 113b represents any other portion.

As described above, in this embodiment, since the wire guide member 101 has each close winding portion 113a and each loose, winding portion 113h, flexibility of the wire guide member 101 changes.

As a result, even if an amount of pulling force of each operation wire 50 increases or return resistance force of the operation wire 50 arranged on the outer side of the bent bending portion 23 is excessive, the wire guide member 101 hardly bends or straightens in the holding member 45 because of the close winding portions 113a, but it smoothly bends. That is, when the bending portion 23 bends, the wire guide member 101 between holding member 41a and holding member 41c and the wire guide member 101 between holding member 41c and holding member 41b smoothly bend without becoming straight. Therefore, the wire guide member 101 does not bent in, for example, holding member 41c, and friction of the operation wire 50 and the wire guide member 101 is alleviated in holding member 45c.

As a result, in this embodiment, when the bending portion 23 bends, the wire guide member 101 can bend in a further smooth arc shape, and the friction of the operation wire 50 and the wire guide member 101 in the holding member 45 can be further dispersed. Furthermore, in this embodiment, a considerable reduction in the working life of the operation wire 50 can be avoided, and the operability of the operation wire 50 can be further improved.

The present invention is not restricted to, the foregoing embodiments as it is, and constituent elements can be modified and embodied in the embodying stage without departing from its gist. Moreover, appropriately combining constituent elements disclosed in the foregoing embodiments results in forming various inventions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A wire guide member which is configured to be held by holding members to allow insertion and forward and backward movement of the wire guide member in the holding members along an axial direction of the holding members, wherein the wire guide member is configured to have inserted therein an operation wire that bends a bending portion and is configured to guide the operation wire, wherein the holding members are arranged in node rings which are adjacent to each other and coupled to each other such that the node rings are movable with a revolving motion to form the bending portion, wherein the node rings include a distal end portion node ring which is at a distal end portion of the bending portion, a proximal end portion node ring which is at a proximal end portion of the bending portion, and at least one intermediate node ring which is between the distal end portion node ring and the proximal end portion node ring, and wherein the holding members include a distal end portion holding member which is arranged in the distal end portion node ring, a proximal end portion holding member which is arranged in the proximal end portion node ring, and an intermediate holding member which is arranged in the intermediate node ring, the wire guide member comprising:
  a small-diameter portion which is configured to be held by the distal end portion holding member, the proximal end portion holding member, and the intermediate holding member to enable the wire guide member to be inserted and moved forward and backward in the distal end portion holding member, the proximal end portion holding member, and the intermediate holding member along the axial direction of the holding members; and
  a plurality of large-diameter portions which have a cross section with a larger diameter than the small-diameter portion and are configured to abut on the distal end portion holding member and the proximal end portion holding member when the bending portion bends, to restrict forward and backward movement of the wire guide member in an axial direction of the wire guide member;
  wherein the large-diameter portions are configured to be arranged on front and rear sides of the distal end portion holding member in such a manner that the large-diameter portions abut on the distal end portion holding member when the bending portion bends and sandwich the distal end portion holding member in the axial direction of the wire guide member in order to restrict movement of the wire guide member toward a distal end portion side and a proximal end portion side of the bending portion when the bending portion bends;
  wherein the large-diameter portions are configured to be arranged on front and rear sides of the proximal end portion holding member in such a manner that the large-diameter portions abut on the proximal end portion holding member when the bending portion bends and sandwich the proximal end portion holding member in the axial direction of the wire guide member in order to restrict the movement of the wire guide member toward the distal end portion side and the proximal end portion side of the bending portion when the bending portion bends; and
  wherein the wire guide member has elasticity.

2. The wire guide member according to claim 1, wherein the small-diameter portion and the large-diameter portion are similar to each other.

3. The wire guide member according to claim 1, wherein the large-diameter portion bulges in at least one direction of radial directions of the wire guide member beyond the small-diameter portion.

4. The wire guide member according to claim 1, wherein the wire guide member comprises a coil spring.

\* \* \* \* \*